United States Patent

Yamada

[11] Patent Number: 5,120,596
[45] Date of Patent: Jun. 9, 1992

[54] COATED BLADE

[75] Inventor: Katsuaki Yamada, Gifu, Japan

[73] Assignee: Kai R&D Center Co., Ltd., Seki, Japan

[21] Appl. No.: 744,658

[22] Filed: Aug. 9, 1991

Related U.S. Application Data

[63] Continuation of Ser. No. 450,469, Dec. 14, 1989, abandoned.

[30] Foreign Application Priority Data

Dec. 15, 1988 [JP] Japan .................. 63-317928

[51] Int. Cl.$^5$ .................. B32B 15/04; B32B 15/08
[52] U.S. Cl. .................. 428/216; 428/336; 428/421; 428/457; 428/463; 428/698; 428/704
[58] Field of Search .............. 428/698, 337, 421, 422, 428/336, 704, 463, 457, 216; 204/192.15; 30/350

[56] References Cited

U.S. PATENT DOCUMENTS 4,470,895  9/1984  Coad et al. .................. 428/698 X
4,843,039  6/1989  Akesson et al. .............. 428/698 X

FOREIGN PATENT DOCUMENTS 56-91742   7/1981  Japan .
62-178970 11/1987  Japan .

Primary Examiner—Thomas J. Herbert, Jr.
Attorney, Agent, or Firm—Oblon, Spivak, McClelland, Maier & Neustadt

[57] ABSTRACT

A coated blade comprising a blade having a surface, and a titanium nitride coating provided on the surface of the blade with a thickness in the range of 0.1 to 0.5 μm. The radius of curvature of a tip portion of the blade is preferably 0.01 to 0.3 μm. A fluororesin coating may be applied on the titanium nitride coating with a thickness not less than 0.1 μm.

11 Claims, 1 Drawing Sheet

● Ceramic Coating (Example 1)
□ Ceramic Coating & PTFE (Example 2)

COATED BLADE

This application is a continuation of application Ser. No. 07/450,469, filed on Dec. 14, 1989, now abandoned.

FIELD OF THE INVENTION

The present invention relates to a blade having the surface coated with ceramic, resin and so on in order to improve the sharpness and corrosion resistance thereof.

DESCRIPTION OF THE RELATED ART

There has been a blade having the surface coated with titanium ceramic in order to improve the sharpness and corrosion resistance thereof. However, the sharpness and corrosion resistance of the blade cannot be improved only by coating the surface with ceramic. The inventors of the present invention have studied to find the following results.

Namely, the thicker the coating of the ceramic is, the better the corrosion resistance of the blade is improved in general. But the sharpness of the blade cannot be improved if the coating is too thick. To the contrary, if the coating is too thin, durability of the coating of the ceramic becomes insufficient in the use of blade, so that the sharpness of the same is easily deteriorated only after a few times of use. Generally speaking, the smaller the radius of curvature of the tip portion of the blade is, the sharper the blade becomes. But where the blade is coated with the ceramic, the coating at the tip portion tends to be thinner than that at another portion in case the radius of curvature of the tip portion is too small. Consequently, the sharpness of the blade cnnot be improved due to such insufficient durability of the ceramic coating.

SUMMARY OF THE INVENTION

An object of the present invention is to provide a coated blade with excellent sharpness and high corrosion resistance, by means of setting a thickness of a film thereof as well as other conditions at optimum in coating the surface with a ceramic and so on.

In order to achieve the above object, the coated blade of the present invention comprises a blade having a surface, and a titanium nitride coating provided on the surface of the blade with a thickness in the range of 0.1 to 0.5 $\mu$m.

Other and further objects of this invention will become obvious upon an understanding of the illustrative embodiments about to be described or will be indicated in the appended claims, and various advantages not referred to herein will occur to one skilled in the art upon employment of the invention in practice.

DETAILED DESCRIPTION OF THE PREFERRED EMBODIMENTS

Figure 1:
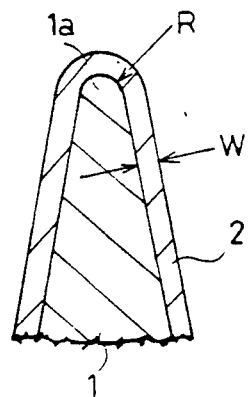
FIG. 1 is a sectional view showing a tip portion of a blade of a surgical knife embodying the present invention.

First and second embodiments of the present invention will be described hereafter referring to FIGS. 1 and 2.

FIRST EMBODIMENT

A blade 1 of a surgical knife made of stainless steel was washed and degreased first, the radius R of curvature of the tip portion 1a thereof being about 0.1 $\mu$m. Then, the blade 1 was set as a sample in an ion plating apparatus, and bombarded for 20 minutes in an argon gas atmosphere of $2 \times 10^{-2}$ torr while rotated so as to clean the surface of the sample. Thereafter, the surface of the sample was coated with a film 2 of titanium nitride (TiN) by means of ion plating method under the following conditions.

That is, nitrogen gas was introduced into the apparatus to form nitrogen gas atmosphere of $5 \times 10^{-4}$ torr. In the same atmosphere, titanium was vaporized at 250° C. through electron beam heating. Then, direct current negative voltage was applied to the sample and ionization of titanium was promoted via a thermoelectron emitter.

Eight samples of the blades 1 each having a coating 2 of titanium nitride (TiN) of a different thickness W were prepared by changing time length of the ion plating. The thickness of the eight samples were 0, 0.1, 0.2, 0.25, 0.3, 0.4, 0.5 and 0.6 $\mu$m. The layer 2 of the thickness W of 0 $\mu$m means that the sample was just washed and degreased. The same sample was used as a comparison sample.

SECOND EMBODIMENT

The same stainless steel blade 1 as the first embodiment, the radius R of curvature of a tip portion 1a of which is about 0.1 $\mu$m, was provided with coatings 2 of titanium nitride (TiN) of different thickness W, thereby to prepare eight samples of layer thickness of 0, 0.1, 0.2, 0.25, 0.3, 0.4, 0.5 and 0.6 $\mu$m. Then, powder of tetrafluoroethylene resin (PTFE) mixed in freon solution was sprayed to the surface of the blades 1 of these eight samples. Each blade 1 was burned at 350° C. in a reducing atmosphere of hydrogen gas to be coated with fluororesin with a thickness of 0.2 $\mu$m. A comparison sample in the present embodiment was a blade 1 which was not provided with titanium nitride coating and was only coated with a fluororesin.

Cut-length tests were performed on each blade 1 of the above first and second embodiments in order to compare the sharpness thereof. The method of cut-length tests is shown as follows.

METHOD OF CUT-LENGTH TESTS

A blade 1 was vertically set on a testing apparatus with a tip portion 1a thereof downward. A polyethylene film of 0.15 mm thickness was rolled around a column of 40 mm diameter provided below the blade 1 so that an axis thereof extended in the horizontal direction. A limit length of the film cut by the blade 1 was measured while pressing the same downward with a load of 100 gram to contact the tip portion 1a with the film around the column, whereas the column was rotated at a predetermined speed (20 mm/sec.).

Figure 2:
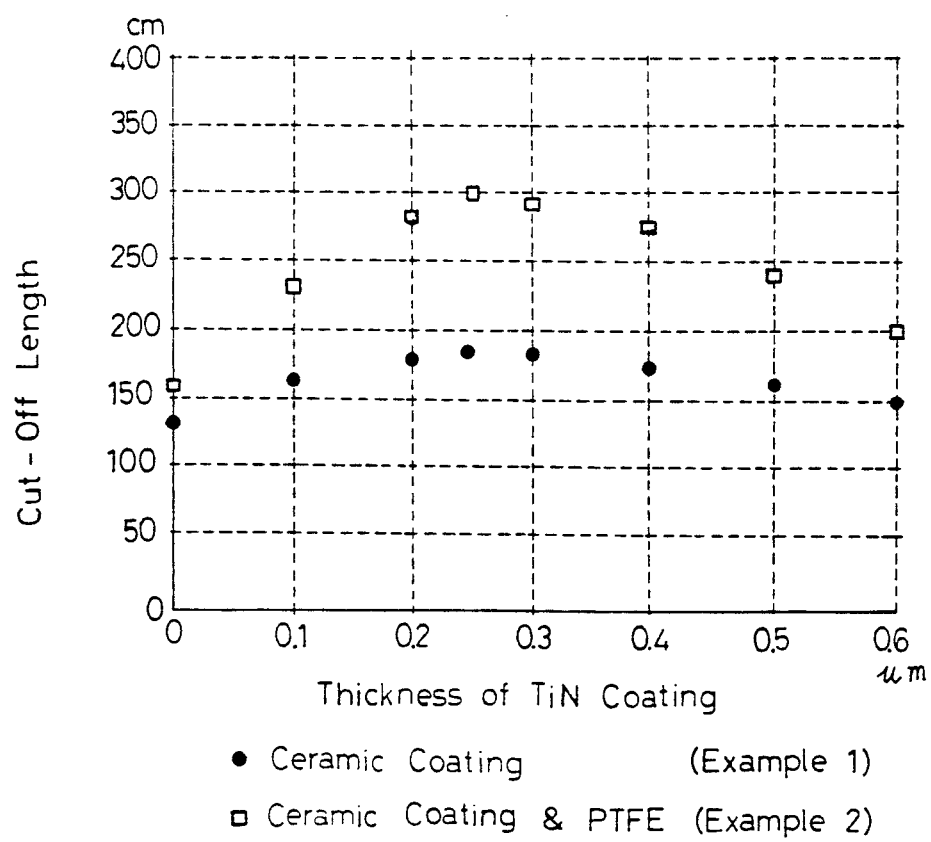
FIG. 2 is a graph showing relationships between the thickness of a titanium nitride film of first and second embodiments and results of cut-length tests.

FIG. 2 shows relationships between the thickness W of the titanium nitride layer 2 of each blade 1 of the first and second embodiments and the cut-length.

As is apparent from FIG. 2, the cut-length is outstandingly long when the thickness W of the titanium nitride film 2 is in the range of 0.1 to 0.5 $\mu$m, compared with the comparison sample which has no titanium nitride coating, with respect to both the first and second embodiments. Comparing these coated blades 1 with unprocessed comparison sample, more that 20% improvement can be seen in their sharpness. A maximal value of cut-length is achieved with the film 2 of the thickness W of around 0.25 μm. If the film thickness W becomes thinner or thicker than this value, the sharpness of the blade 1 tends to be lowered. This is possibly because the hardness of the blade surface gets better in the above range of the layer thickness W, without any affection to the sharpness thereof.

Comparing the first and second embodiments with each other at each coating thickness, the cut-length of the second embodiment blade 1 always longer than that of the first embodiment. This means that the sharpness of the titanium nitride coated blade 1 becomes improved even better in the case of being further coated with the tetrafluoroethylene resin. This is considered to be because the lubricating ability of the fluororesin lowers the cutting resistance. In respect of the tetrafluoroethylene resin flim, the thickness of not less than 0.1 μm makes improved the sharpness of the blade. If the thickness is less than that value, the durability of the same film becomes insufficient and the sharpness gets affected even in a few times of use of the blade 1.

The blades 1 of the first and second embodiments, moreover, have an excellent corrosion resistance against fat, blood, etc. owing to the titanium nitride coating 2. Especially, as for the blade 1 of the second embodiment, the corrosion resistance is made better because of characteristics of the fluororesin.

In the above second embodiment, the tetrafluoroehylene resin (PTFE) was used as a fluororesin, but other kinds of fluororesin may be used, such as a chlorotrifluoroethylene resin, a fluorovinylidene resin, or the like.

In the application of the titanium nitride film 2 of the above first and second embodiments, the optimal radius R of curvature of the tip portion 1a of the blade 1 is 0.01 to 0.3 μm. The sharpness of the blade 1 cannot be improved if the radius R of curvature is less than 0.01 μm since the titanium nitride coating of enough thickness is not able to be formed. If the radius R of curvature is more than 0.3 μm, the sharpness of the blade 1 is deteriorated and lowered.

As many apparently widely different embodiments of this invention may be made without departing from the spirit and scope thereof, it is to be understood that the invention is not limited to the specific embodiments thereof except as defined in the appended claims.

what is claimed is:

1. A coating cutting blade comprising:
    a stainless steel blade substrate having a cutting surface; and
    a titanium nitride coating provided directly on the cutting surface of the blade, the titanium nitride coating having a thickness of at least 0.1 μm to 0.5 μm.

2. A coated cutting blade according to claim 1, wherein said cutting surface includes a cutting edge having a radius of curvature in the approximate range of 0.01 of 0.3 μm.

3. A coating cutting blade as recited in claim 1 wherein titanium nitride coating is formed by ion plating.

4. A coated cutting blade as recited in claim 1 wherein the titanium nitride coating has thickness in the range of approximately 0.2 to 10.4 μm.

5. A coated cutting blade as recited in claim 1 wherein the titanium nitride coating has a thickness of approximately 0.25 μm.

6. A coated cutting blade as recited in claim 5 wherein said coated blade is a surgical knife.

7. A coated cutting blade comprising:
    a stainless steel blade substrate having a cutting surface;
    a titanium nitride coating provided directly on the cutting surface of the blade, the titanium nitride coating having a thickness in the approximate range of 0.1 to 0.5 μm; and
    a fluororesin coating applied on the titanium nitride coating, the fluororesin coating having a thickness of at least approximately 0.1 μm.

8. A coated cutting blade as recited in claim 7 wherein the titanium nitride coating has a thickness in the range of approximately 0.2 to 0.4 μm.

9. A surgical knife comprising:
    a stainless steel blade substrate having a cutting surface that includes a cutting edge having a radius of curvature in the approximate range of 0.01 to 0.3 μm:
    a titanium nitride coating formed on the cutting surface of the blade by ion plating, the titanium nitride coating having a thickness in the range of approximately 0.1 to 0.4 μm; and
    a fluororesin coating applied on the titanium nitride coating, the fluororesin coating having a thickness of at least approximately 0.1 μm.

10. A surgical knife as recited in claim 9 wherein the titanium nitride coating has a thickness in the range of approximately 0.2 to 0.4 μm.

11. A surgical knife as recited in claim 9 wherein the titanium nitride coating has thickness of approximately 0.25 μm.

* * * * *